United States Patent [19]

Tokumaru

[11] Patent Number: 5,477,328
[45] Date of Patent: Dec. 19, 1995

[54] OPTICAL TRANSMISSION CALIBRATION DEVICE AND METHOD FOR OPTICAL TRANSMISSIOMETER

[75] Inventor: Syokichi Tokumaru, Tokyo, Japan

[73] Assignee: OKI Electric Industry Co., Ltd., Tokyo, Japan

[21] Appl. No.: 230,406

[22] Filed: Apr. 20, 1994

[30] Foreign Application Priority Data

Apr. 27, 1993 [JP] Japan ................................. 5-101000

[51] Int. Cl.$^6$ ................................................. G01N 21/59
[52] U.S. Cl. ................................... 356/437; 356/434
[58] Field of Search ........................... 356/433, 434, 356/435, 437, 438, 439

[56] References Cited

U.S. PATENT DOCUMENTS 3,872,315  3/1975  Boll .................................. 356/439
4,560,873  12/1985  McGowan et al. .
4,726,684  2/1985  Tokumaru .
5,028,790  7/1991  McGowan et al. .

Primary Examiner—Richard A. Rosenberger
Attorney, Agent, or Firm—Steven M. Rabin

[57] ABSTRACT

An optical transmission measurement apparatus has a pair of a transmitter/receiver units, beam splitters, and a reflection mirror block on both sides of an object of an atmosphere whose optical transmission factor is to be measured. Each of the transmitter/receiver units comprises a light source which can adjust the optical energy of its emitted light beam. A first beam splitter which the light beam enters after the emission, diverges the light beam into two components with different polarizations. After the divergence, during optical transmission measurement, one of the two diverged components enters the opposite photo-detector, while the other of the components returns to the photo-detector in the same unit as the light source which emitted the light beam, by being reflected thereto with the second beam splitter. On the other hand, during calibration, one of the two diverged components is reflected at the reflection mirror block to enter the photo-detector in the same unit as the light source which emitted the light beam, while the other of the components returns to the photo-detector in the same transmitter/receiver unit as that which emitted the light beam, by being reflected with the second beam splitter.

16 Claims, 10 Drawing Sheets

OPTICAL TRANSMISSION CALIBRATION DEVICE AND METHOD FOR OPTICAL TRANSMISSIOMETER

CROSS REFERENCE TO RELATED APPLICATION

This application claims the priority benefits of Japanese application No. 101000/1993, filed Apr. 27, 1993, the entire disclosure of which is incorporated herein by reference.

BACKGROUND OF THE INVENTION

The present invention relates to a calibration method for measuring an optical transmission factor of exhaust gas or contaminated atmosphere. The present invention has an application, for instance, in a smoke indicator, a dust concentration indicator, or a gas combustion control, etc.

The present invention provides some considerable improvement on the optical transmission measurement apparatus being disclosed in U.S. Pat. No. 4,726,684, which was invented by the same inventor and has been assigned to the assignee of the present invention.

In the '684 patent, the inventor of the present invention has disclosed an original measurement device and method that measures the optical transmission factor with a pair of intercommunicating laser beams.

In this patent, it is an essential process to detect how much of the optical energy of each of the laser beams is reduced as the beams pass through exhaust gas, combustion gas, or other object. And it is another essential process to provide an indication of how much of each of the laser beams goes through the object when the object does not disturb the laser beams.

Practically in the apparatus, a pair of photo-detectors detect the optical energies of the laser beams which have passed through the object. By the detection, the optical transmission factor of the object would be determined as a relative percentage between 0 and 100%. So, in order to determine the relative percentage, the levels of the output signals from the photo-detectors should be predetermined, according to the reduction of the energy of the laser beams under two different conditions. One of the two conditions is where the object does not disturb the laser beams. The other condition is where the laser beams do not reach the photo-detectors because the laser beams are completely shut out by the object.

In order to determine the levels of the signals, one simple technique is to examine the output signals when the laser beams approach the photo-detectors directly without any reduction, and when the laser beams do not reach the photo-detectors. For providing these conditions, one way is for the object to be clear fresh air, a path through which can be blocked with an opaque light-disturbing device.

However, it is a technical problem that the optical energies of the laser beams are reduced not only through the object, but also in interactions with other optical devices. One of those devices is the polarized beam splitter. Although the optical reduction factor of the polarized beam splitter itself is determinate, the optical reduction factor of dirt, blurs, or scratches on the surface of the polarized beam splitter is indeterminate, or unclear. The condition of the beam splitter will change during the measurement because the air to be measured will provide some dust or soil on the beam splitter surface, or cause the beam splitter itself to deteriorate over time.

Those optical reductions in the polarized beam splitter will disturb the determination of the exact relative optical transmission by biasing the standard condition of zero reduction, or that of complete reduction, of the optical energies of the laser beams.

In addition, it is another problem that providing clean air during the measurement is very troublesome. In order to provide clean air in place of the object, it is necessary to remove the exhaust gas to be measured. Upon removing the air to be measured, it becomes impossible to measure the optical transmission factor. Removing the exhaust gas completely enables calibration to be performed. After the calibration, the clean air must be replaced with the exhaust gas to be measured again.

Thus, in the air replacing process described above, great difficulties cannot be avoided.

In order to avoid those difficulties concerned with the calibrations, the present invention will provide an advanced calibration device and a simple calibration process for the apparatus of the '684 patent.

One purpose of the present invention is to provide an advanced optical transmission apparatus and method that enables the calibration to be performed without replacing exhaust gas with clean air.

Another purpose of the present invention is to provide an advanced optical transmission apparatus and method that enables a speedy calibration that takes only a short time during the measurement.

And still another purpose of the present invention is to provide an advanced optical transmission apparatus and method that enables an automatic calibration to be performed without manual operation, that is of great help for maintaining accuracy during long term continuous measurement.

SUMMARY OF THE INVENTION

In order to achieve the purpose of the invention, there is provided a pair of reflection mirror blocks which have reflection means that reflect laser beams. The reflection mirror blocks are inserted into the laser beam paths between the polarized beam splitters and an object to be measured, and completely reflects the laser beam being emitted from one polarized beam splitter to another polarized beam splitter on the same side of the object, thereby keeping the light beams from the object.

With the reflection mirror blocks in place, each of the laser beams passes through one polarized beam splitter, reflects off the reflection mirror block, then returns to the other polarized beam splitter on the same side as the first polarized beam splitter, and reaches the photo-detector.

Then the photo-detector detects the laser beam with a reduction in optical energy substantially limited to that caused by the first and second polarized beam splitters, without any affect by the object, and generates accurate calibration signals according to the detected laser beams.

DESCRIPTION OF THE PREFERRED EMBODIMENTS

Figure 1A:
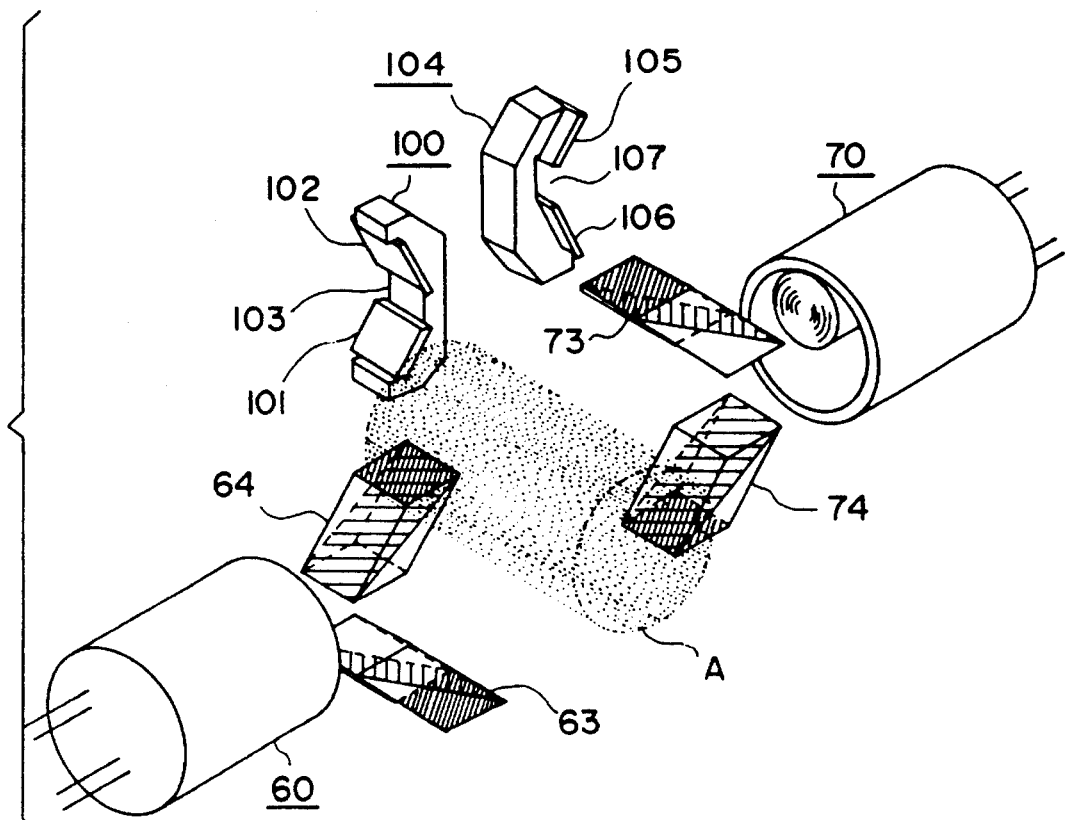
FIGS. 1a and 1b show the optical transmission measurement apparatus of the present invention.
Figure 1B:
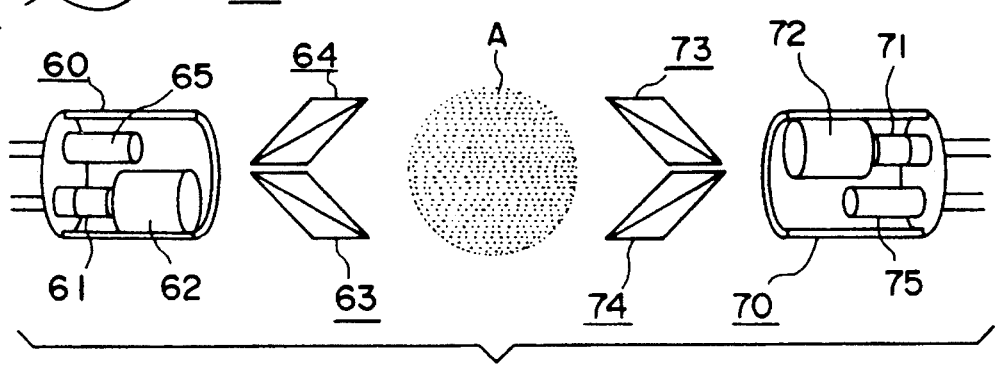

FIGS. 1a and 1b show a preferred embodiment of the present invention.

FIGS. 1a and 1b show the transmitter/receiver units 60 and 70 are facing each other in the apparatus. Those transmitter/receiver units 60 and 70 are facing so that each unit can direct light beams into the other unit. The characteristics of the light beam will be described below.

Between the transmitter/receiver units 60 and 70 is an object A. This object A comprises an atmosphere whose optical transmission factor is to be detected in a flue.

In the embodiment, the object A is placed where the object A overlaps the light beam paths emitted from the transmitter/receiver units 60 and 70.

Figure 8:
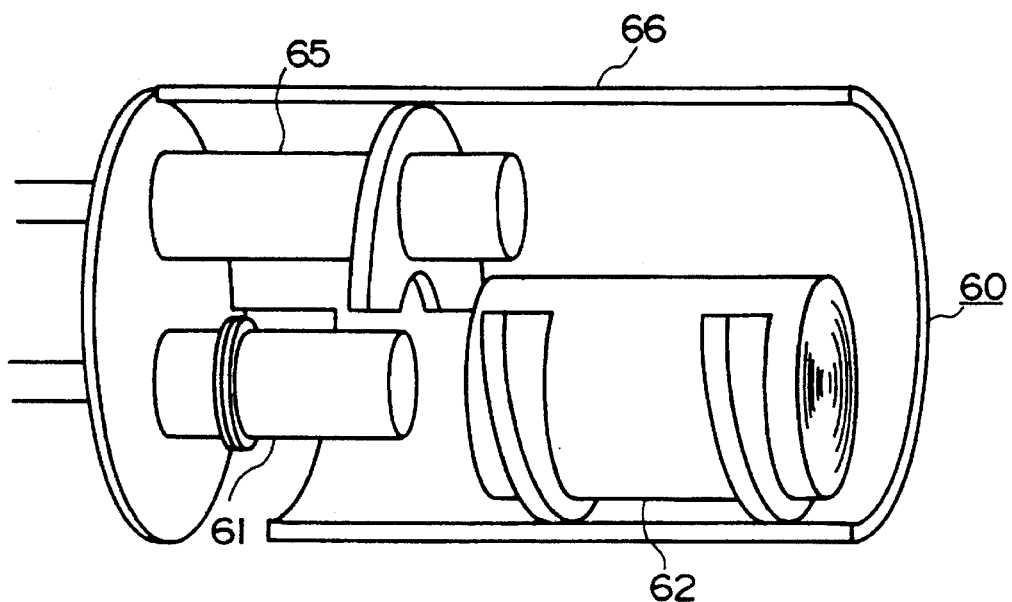
FIG. 8 is a partially cut away view of the transmitter/receiver unit 60.

FIG. 8 shows the the construction of the transmitter/receiver unit 60. The transmitter/receiver unit 60 comprises a cylindrical housing 66. The housing 66 has an opening on one side. Inside the housing 66 is placed a light source 61 so that the light source can provide a light beam through the opening of the housing 66.

Figure 7A:
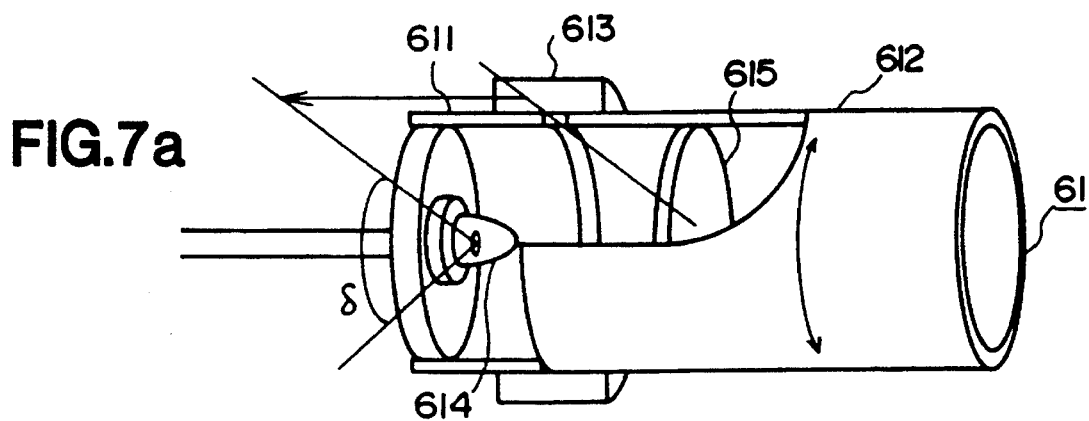
FIGS. 7a–7d are partially cut away views of the light sources 61,71, and the photo-detectors 65, 75.

The structure of the light source 61 is shown in FIG. 7a. In the light source 61, the cylindrical housing comprises two parts, including a fixed part 611 and a rotatable part of 612. Those two parts 611 and 612 are rotatably joined by a ring joint 613, so that the rotatable part 612 can rotate around its axis. In the fixed part 611 is mounted a laser diode 614 which has a predetermined polarization angle. In the rotatable part 612 is mounted a polarization filter 615. The polarization film 615 is mounted so that the laser beam being emitted from the laser diode 614 goes through the object A. Also, the polarization filter 615 rotates together with the rotatable part 612. So, the polarization angle of the laser diode 614 and the polarization surface of the polarization filter 615 define a certain polarization angle δ. According to the polarization angle δ, the optical energy of the laser beam through the polarization filter will be reduced. The percentage of reduction will depend on the polarization angle δ. When the value of δ is 0°, the optical energy of the laser beam is not reduced at all; when the value of δ is 90°, the optical energy of the laser beam completely vanishes. As a result, the optical energy of the laser beam being emitted from the light source 61 is adjustable by rotating the rotatable part 612.

As shown in FIG. 8, next to the light source 61 is a lens assembly 62. It comprises a single lens or a set of lenses. It shares the same optical axis as the light source 61. The lens assembly 62 transfers the light beam emitted from the light source 61 as a parallel beam. It also restricts the light beam diameter to less than the minimum effective diameter of the first or second beam splitter which will be described below.

The first beam splitter 63 is placed in the transmitter/receiver unit 60. This first beam splitter 63 is placed on the path of the light beam emitted from the lens assembly 62.

Also in FIG. 1b, the shape of the first beam splitter 63 is illustrated. As shown, the first beam splitter 63 has a parallelogram shape in section.

Figure 2:
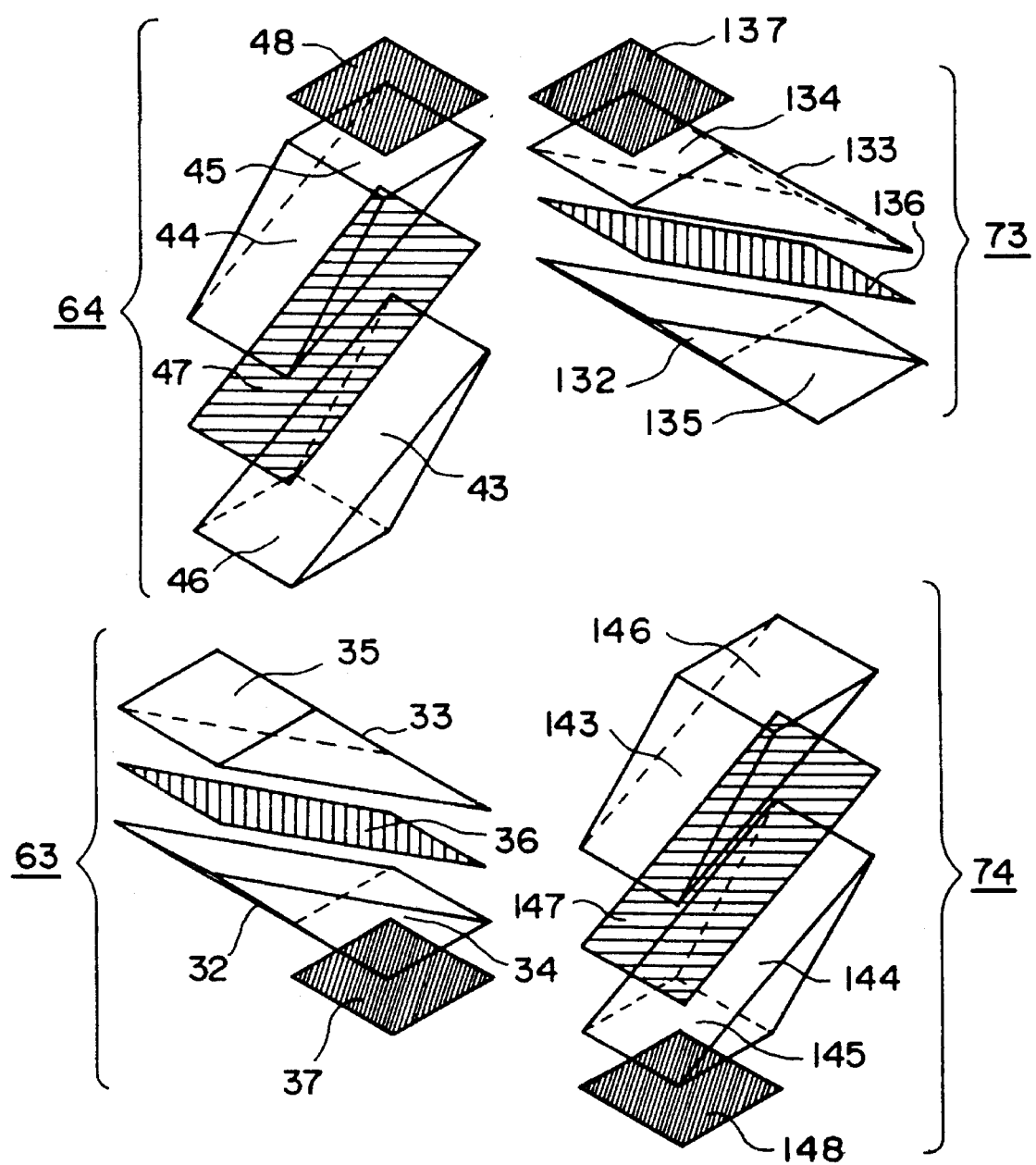
FIG. 2 is an exploded view of the polarized beam splitters.

Referring to FIG. 2, the first beam splitter 63 has two pairs of surfaces which are parallel to each other, namely one pair of surfaces 32 and 33, and another pair of surfaces 34 and 35. On the surface 34 is attached a reflection film 37, which reflects a light beam inside the first beam splitter 63. The other three surfaces 32, 33, and 35 are transparent so that light beams can pass through those surfaces.

In addition, a diagonal surface comprises a polarization film 36. The polarization film 36 diverges a light beam into plurality of light components by its polarization surfaces.

Figure 4A:
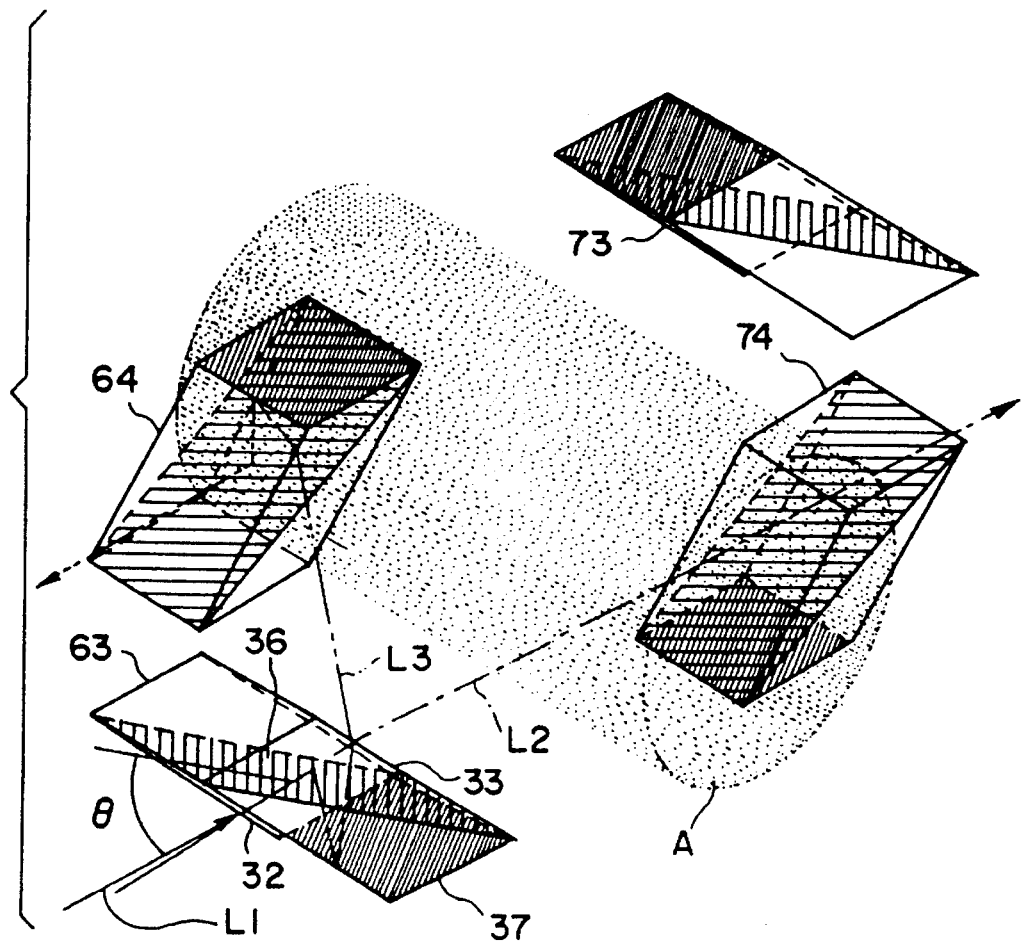
FIGS. 4a and 4b show the light beam paths of the P component and S component being emitted from the light source 61.

The polarization film 36 is in a plane disposed at a Brewster angle θ to the entering light beam from the lens assembly 62, as is shown in FIG. 4a. The Brewster angle is generally well known to be one at which the light beam enters the polarization film in order that it will diverge into two light components which have the same energies.

Objectively, the Brewster angle is not fixed but depends on a characteristic of the polarization film and on the beam splitter material.

Near the first beam splitter 63 is a second beam splitter 64.

The second beam splitter 64 is placed where one of the diverged light components emitted from the first beam splitter 63 can enter. The diverged light component will be described below.

The second beam splitter 64 has a construction similar to that of the first beam splitter 63. The construction of the second beam splitter 64 is also shown in FIG. 2.

As shown in FIG. 1b, the second beam splitter 64 also has a parallelogram shape in sectional view.

The second beam splitter 64 has two pairs of surfaces which are parallel to each other, including one pair of surfaces 43 and 44, and another pair of surfaces 45 and 46. On the surface 45 is attached a reflection film 48, which reflects a light beam inside the second beam splitter 64. The other three surfaces 43, 44, and 46 are transparent so that light beams can pass through those surfaces.

In addition, a diagonal surface comprises a polarization film 47. The polarization film 47 causes a light beam to diverge into plurality of light components, by its polarization surfaces.

The second beam splitter 64 is placed where it makes the light beam that enters from the first beam splitter 63 take the same light path as another light beam that enters from the transmitter/receiver unit 70.

The light beam entering from the transmitter/receiver unit 70 will be described below.

Figure 6:
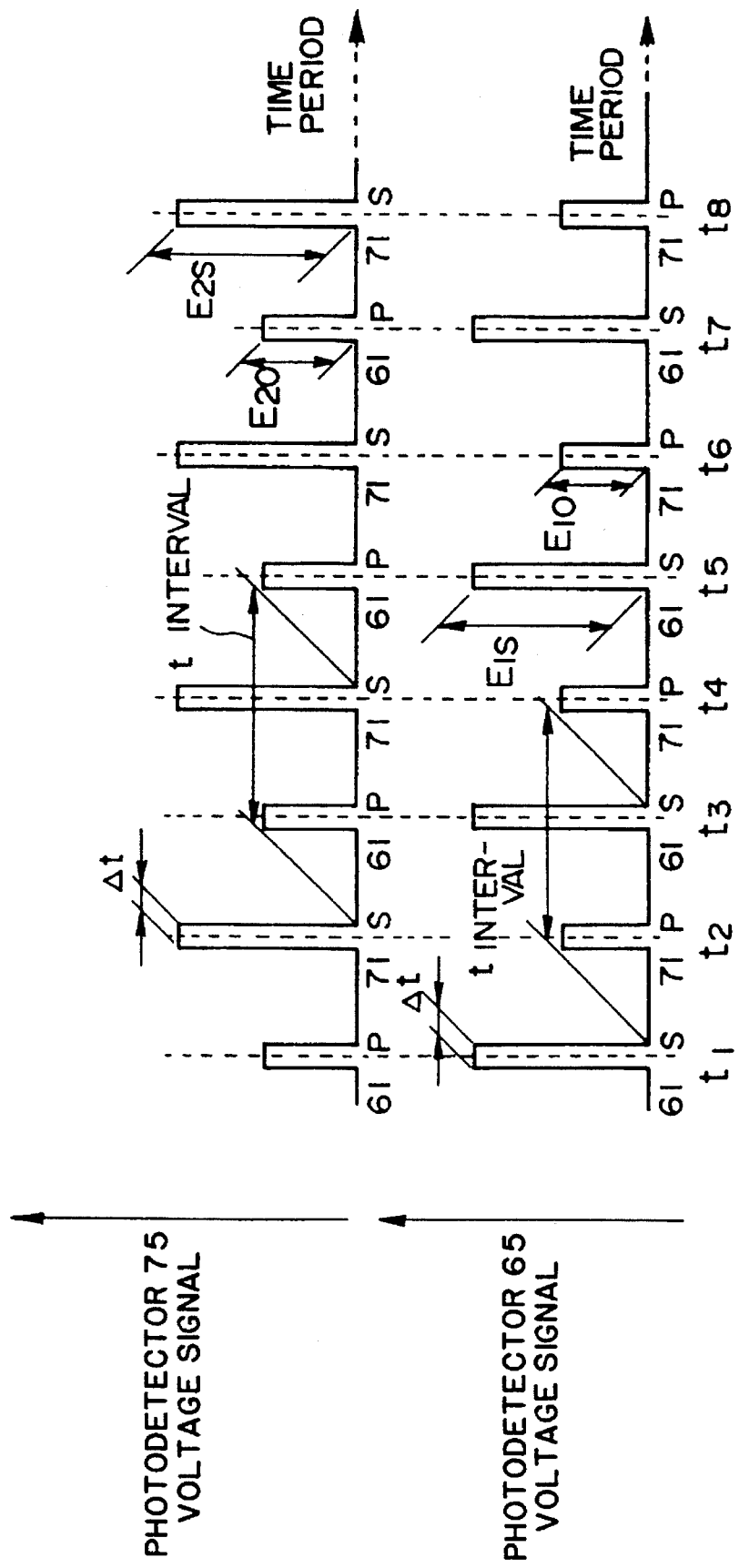
FIG. 6 is a time chart of the output signals from the photo-detectors corresponding to the light beams as they reach the photo-detectors.

The last device in the transmitter/receiver unit 60, shown in FIG. 1b, is the photo-detector 65. The photo-detector 65 consists of, for example, a CdS cell. The photo-detector 65 generates a voltage signal as shown in FIG. 6, in response to receiving a light beam. The voltage of the signal is in proportion to the energy of the light beam. Objectively, it will be easily achieved by rotating the rotatable part 612 of the light source 61 by an accurate angle.

Figure 11A:
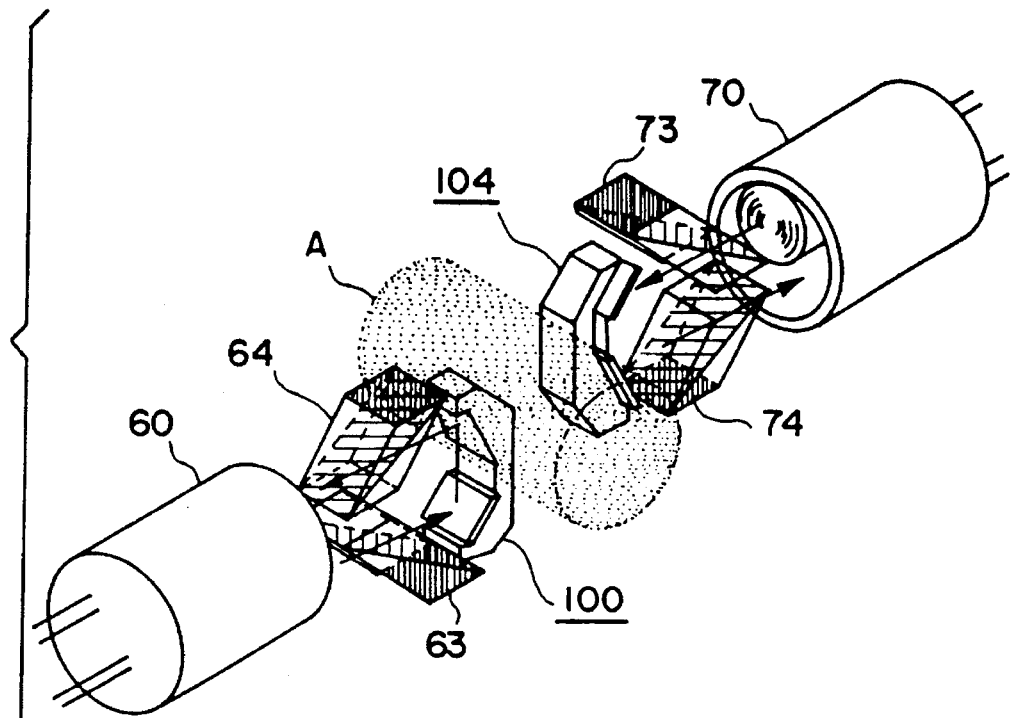
FIGS. 11a and 11b show the optical transmission measurement apparatus in a condition for performing a span calibration.
Figure 11B:
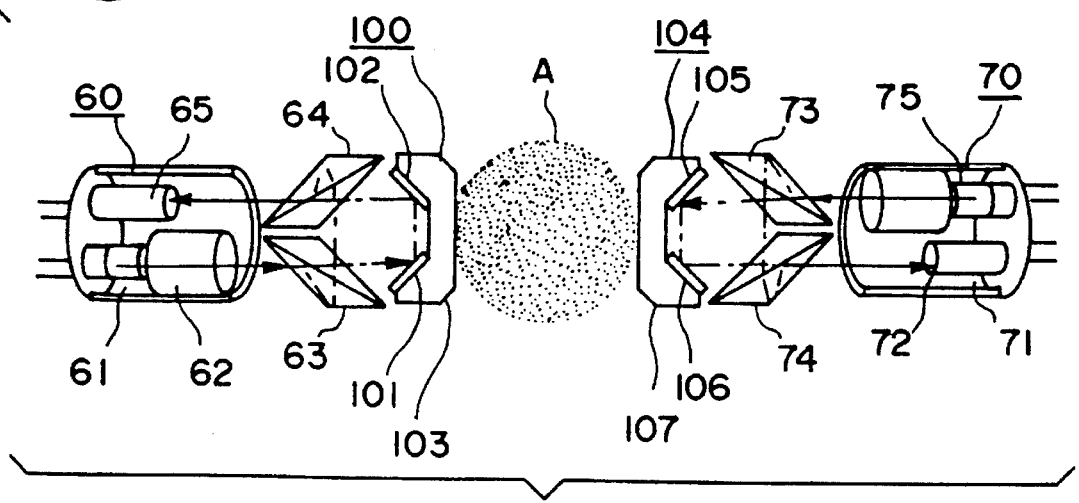

In FIGS. 11a and 11b, a reflection mirror block 100 is placed between the object A and the polarized beam splitter 63, and between the object A and the polarized beam splitter 64.

The reflection mirror block 100 can slide into and out of the path of the light beam emitted from the transmitter/receiver unit 60, in a direction perpendicular to the path, so that the reflection mirror block will interrupt the light beam, or allow the light beam to pass through the object A.

Figure 9A:
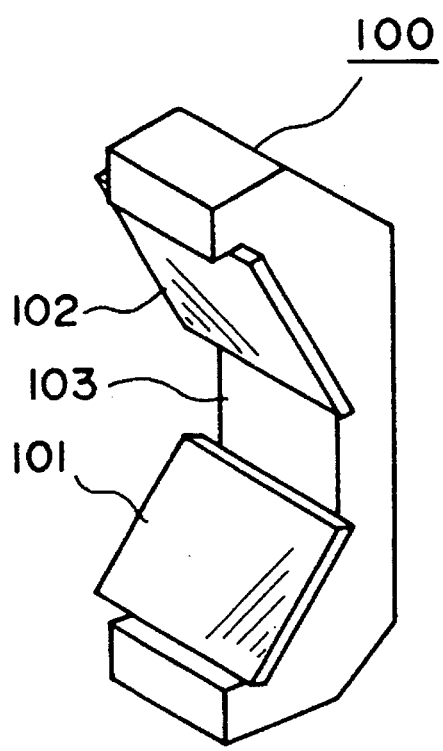
FIGS. 9a and 9b show the respective structures of the reflection mirror blocks 100 and 104.
Figure 9B:
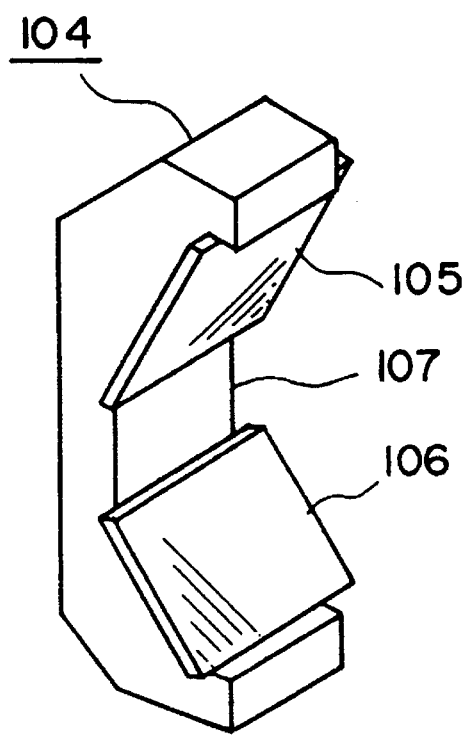

FIG. 9a is a perspective view of the reflection mirror block 100. The reflection mirror block 100 comprises a first reflection mirror 101 and a second reflection mirror 102, both of which are mounted on a mirror mount block 103. Those two reflection mirrors 101 and 102 fully reflect entering light beams, and are mounted so as to be spaced from each other by the same distance as that by which the two light beams emitted from the transmitter/receiver unit 60 and the transmitter/receiver unit 70 are spaced from each other.

The first reflection mirror 101 is mounted to receive the light beam at a 45° angle, when the reflection mirror block 100 is slid into position in the path of the light beam emitted from the transmitter/receiver unit 60, wherein the second reflection mirror 102 is mounted perpendicularly to the first reflection mirror 101, to face the first reflection mirror 101.

As shown in the FIGS. 11a and 11b, when the reflection mirror blocks 100 and 104 are disposed on the light paths between the transmitter/receiver unit 60 and beam splitters 63, 64, the first reflection mirror 101 will be inserted between the lens assembly 62 and the first beam splitter 63, while the second reflection mirror 102 will be inserted between the photo-detector 65 and the second beam splitter 64.

Figure 10:
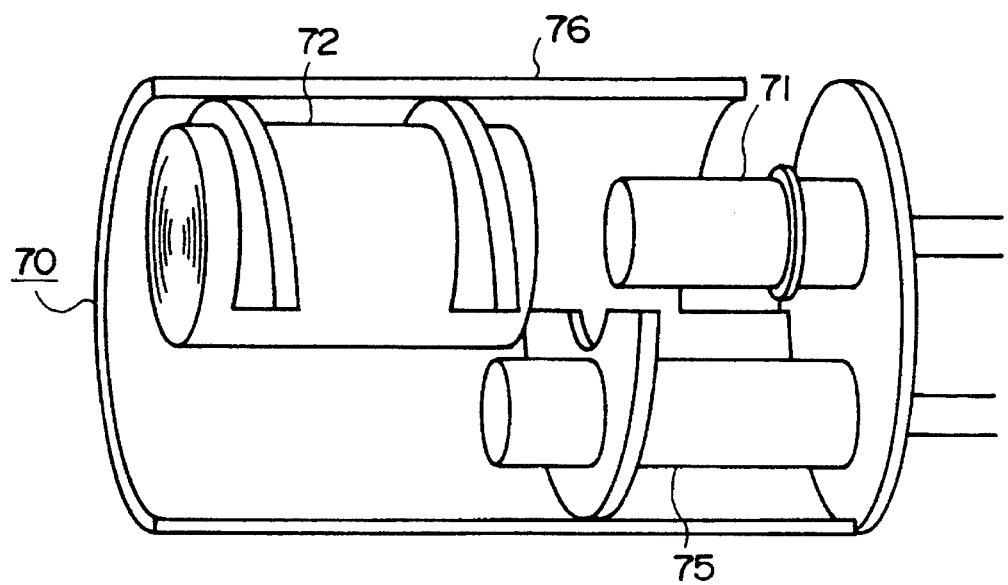
FIG. 10 is a partially cut away view of the transmitter/receiver unit 70.

FIG. 10 shows the structure of the transmitter/receiver units 70. The transmitter/receiver units 70 comprises a light source 71, a lens assembly 72, a third beam splitter 73, a fourth beam splitter 74, and a photo-detector 75. The photo-detector 75 consists of, for example, a CdS cell, as is the photo-detector 65.

The light source 71 is a laser diode or a similar light emitting device. The light beam emitted from the light source 71 has a narrow wavelength band, and a constant optical energy.

Figure 7B:
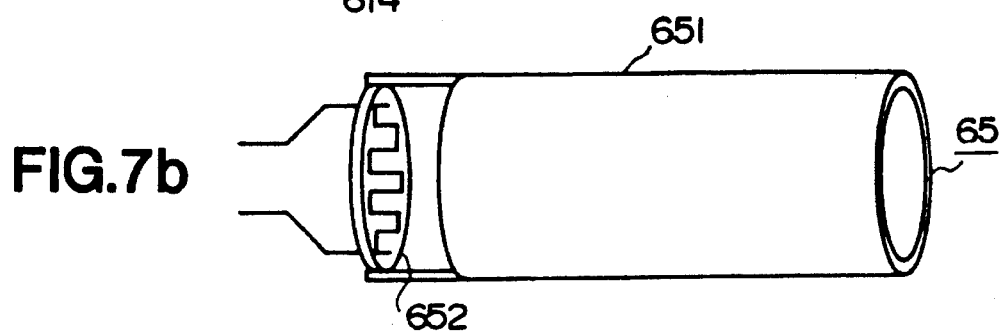
Figure 7C:
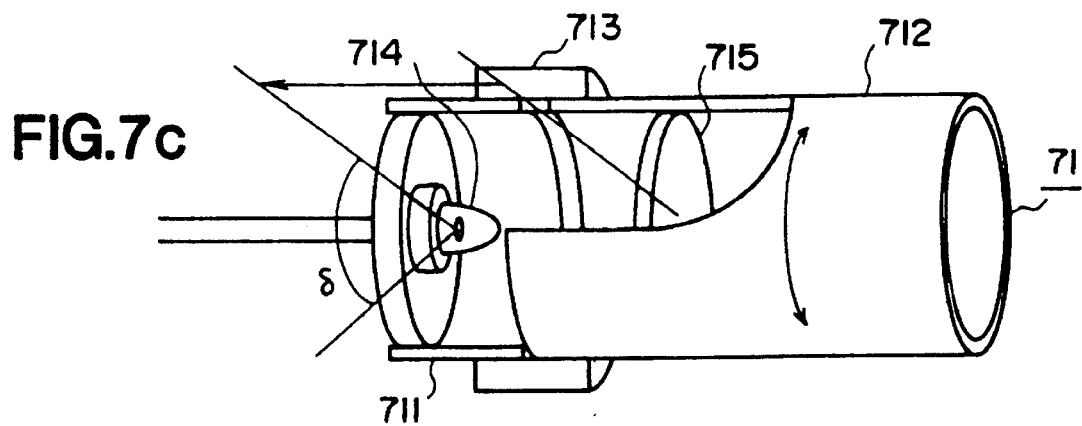
Figure 7D:
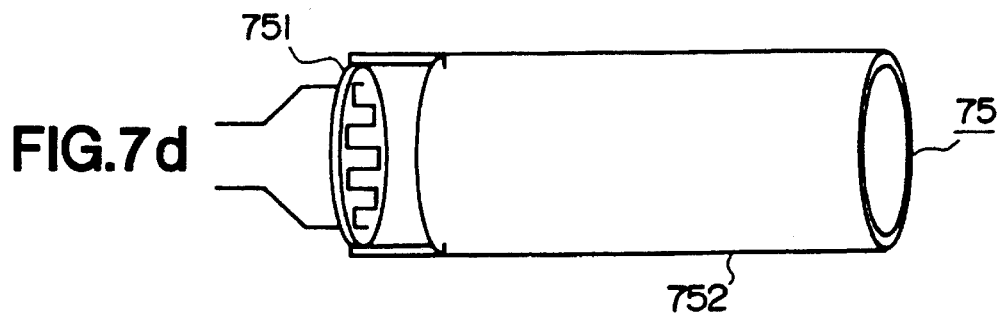

The light source 71 is shown in FIG. 7b. In the light source 71, the cylindrical housing comprises two parts, including a fixed part 711 and a rotatable part 712. Those two parts 711 and 712 are rotatably joined by a ring joint 713, so that the rotatable part 712 can rotate around its axis. In the fixed part is mounted a laser diode 714 which has a predetermined polarization angle. In the rotatable part 712 is mounted a polarization film 715. The polarization film 715 is mounted so that the optical energy of the laser beam being emitted from the laser diode 714 can be varied. Also, the polarization film 715 rotates with the rotatable part 712. So, the polarization angle of the laser diode 713 and the polarization surface of the polarization film 715 define a certain polarization angle $\delta$. According to the polarization angle $\delta$, the optical energy of the laser beam through the polarization filter 715 will be reduced. The percentage of reduction will depend on the polarization angle $\delta$. As a result, the optical energy of the laser beam being emitted from the light source 71 can be changed by rotating the rotatable part 712.

The third beam splitter 73 is placed in the transmitter/receiver unit 70. This third beam splitter 73 is placed on the path of the light beam emitted from the lens assembly 72.

In FIG. 1b, a cross-sectional view of the third beam splitter 73 is illustrated. As shown, the third beam splitter 73 has a parallelogram shape in section.

Referring to FIG. 2, the third beam splitter 73 has two pairs of surfaces which are parallel to each other, including one pair of surfaces 132 and 133, and another pair of surfaces 134 and 135. On the surface 134 is attached a reflection film 137, which reflects a light beam inside the third beam splitter 73. The other three surfaces 132, 133, and 135 are transparent so that light beams can pass through those surfaces.

In addition, a diagonal surface comprises a polarization film 136. The polarization film 136 causes a light beam to diverge into plurality of light components, by its polarization surfaces.

The polarization film 136 is in a plane at a Brewster angle $\theta$ to the entering light beam from the lens assembly 72 so that the entering light beam, upon incidence with the polarization film, diverges into two light components which have the same energy.

Objectively, the Brewster angle is not fixed but depends on a characteristic of the polarization film and on the beam splitter material.

Near the third beam splitter 73 is the fourth beam splitter 74.

The fourth beam splitter 74 is placed to receive one of the diverged light components emitted from the third beam splitter 73. That diverged light component will be described below.

The fourth beam splitter 74 is structurally similar to the third beam splitter 73, as is shown in FIG. 2.

As shown, the fourth beam splitter 74 also has a parallelogram shape in sectional view.

The fourth beam splitter 74 has two pairs of surfaces which are parallel to each other, including one pair of surfaces 143 and 144, and another pair of surfaces 145 and 146. On the surface 145 is attached a reflection film 148, which reflects a light beam inside the fourth beam splitter 74. The other three surfaces 143, 144, and 146 are transparent so that light beams can pass through those surfaces.

In addition, a diagonal surface comprises a polarization film 147. The polarization film 147 causes a light beam to diverge into plurality of light components, by its polarization surfaces.

The fourth beam splitter 74 is placed where it makes the light beam that enters from the third beam splitter 73 take the same light path as another light beam that enters from the transmitter/receiver unit 60.

The last device in the transmitter/receiver unit 70 is the photo-detector 75. The photo-detector 75 generates a voltage signal in response to receiving a light beam. The voltage of the signal is in proportion to the energy of the light beam.

In FIGS. 11a and 11b, another reflection mirror block 104 is shown placed between the object A and the beam splitters 73 and 74.

As shown in FIGS. 11a and 11b, the reflection mirror block 104 can slide into and out of the path of the light beam emitted from the transmitter/receiver unit 70 in a direction perpendicular to the path, so that the reflection mirror block will interrupt the light beam, or allow the light beam to pass through the object A.

The reflection mirror block 104 comprises a first reflection mirror 105 and a second reflection mirror 106, both of which are mounted on a mirror mount block 107. Those two reflection mirrors 105 and 106 fully reflect entering light beams, and are mounted spaced from each other the same distance as that between the two light beams which are emitted from the transmitter/receiver unit 60 and the transmitter/receiver unit 70.

The first reflection mirror 105 is mounted to receive the light beam at a 45° angle, when the reflection mirror block 104 is slid into position in the path of the light beam emitted from the transmitter/receiver unit 60, wherein the second reflection mirror 106 is mounted perpendicularly to the first reflection mirror 105, to face the first reflection mirror 105.

As shown in FIGS. 11a and 11b, when the reflection mirror block is moved into position between the object A and the beam splitters 73, 74, the first reflection mirror 105 will be inserted between the lens assembly 72 and the third beam splitter 73, while the second reflection mirror 106 will be inserted between the photo-detector 75 and the fourth beam splitter 74.

The operation of those devices in the apparatus of the disclosed embodiment will be described hereinafter.

Figure 3:
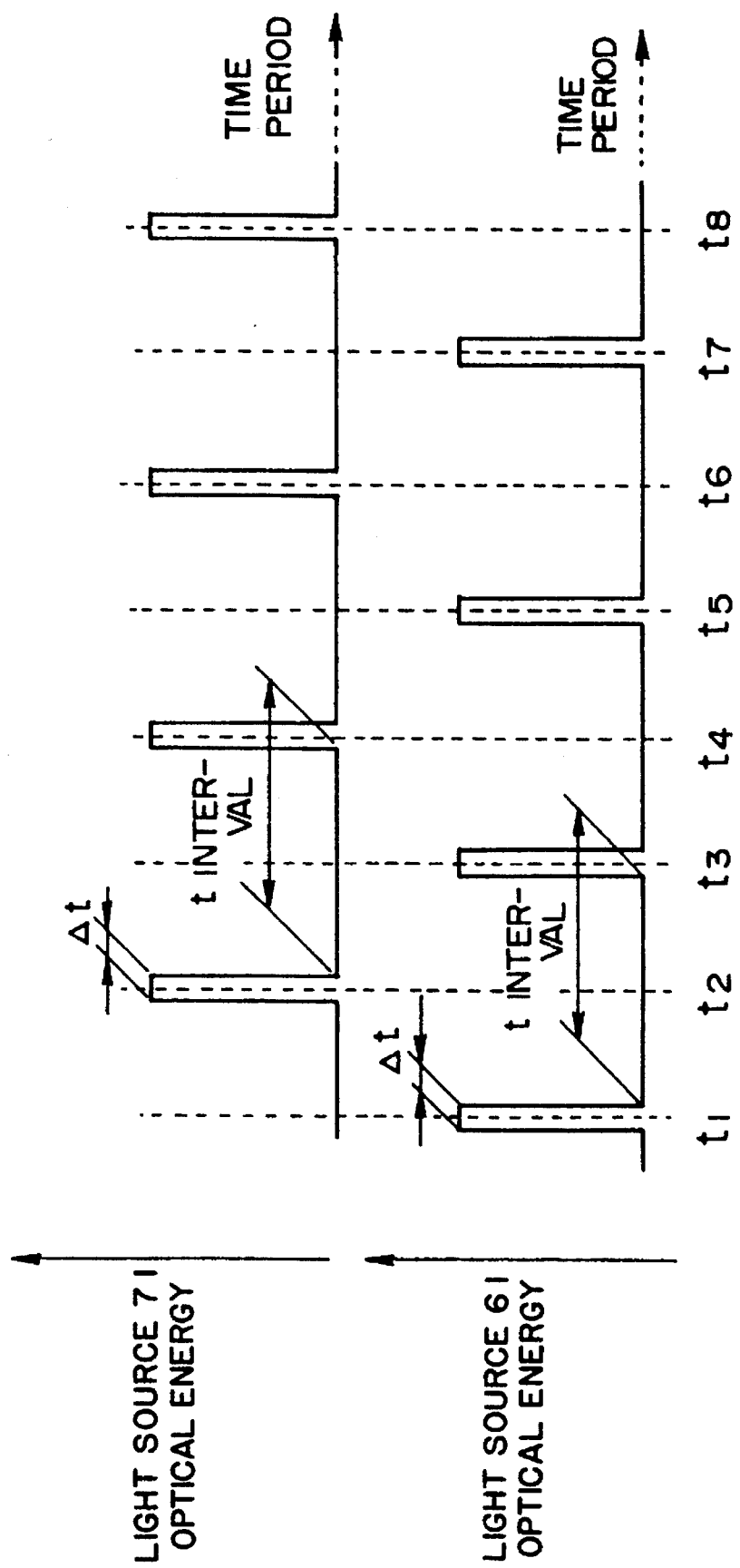
FIG. 3 is a time chart showing the timing of emissions from the light sources on the both sides of the optical transmission apparatus.

FIG. 3 visually shows a time chart of light emission at the light source 61 and 71. In the chart, the vertical scale shows optical energy of the light beams being emitted from each light source, while the horizontal scale shows the time period.

As shown, the light source 61 intermittently emits light beam pulses of time duration $\Delta t$ and constant optical energy, with regular absence of light of time duration $t_{interval}$, in the transmitter/receiver unit 60. On the other hand, the other light source 71 also intermittently emits light beam pulses in the transmitter/receiver unit 70, during the periods of absence of the light emission from the light source 61.

As can be understood from the explanation above or from FIG. 6, it is less than half of the total time period that each of the light source emits a light beam. And the light sources 61 and 71 never emit light beams simultaneously. This characteristic of the timing of light beam emissions aims to avoid the P component from the light source 61 and S component from the light source 71 being mixed at the photo-detector 75, and as well to avoid the P component from the light source 71 and S component from the light source 61 being mixed at the photo-detector 65.

In order to simplify the explanation, the best example of the essential operation will be described hereinafter, as to the left side of the object A first. Of course, the same or similar operation will be carried out on the other side of the object A.

The light beam emitted from the light source 61 has a single narrow wavelength band. It is preferably a nondiffused beam, such as a laser beam.

The light beam enters the lens assembly 62 and is output as a parallel light beam.

The lens assembly 62 also restricts the light beam diameter to be smaller than the effective diameter of the first or second beam splitter 63 or 64. The restriction helps to prevent the light beam from diffusing, when the light beam enters the beam splitters 63 and 64.

Figure 4B:
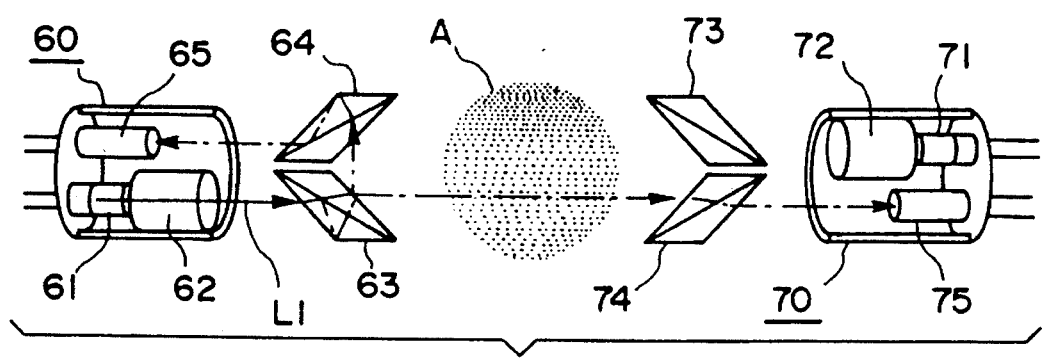

Upon exiting the lens assembly 62, the light beam enters the first beam splitter 63 at the transparent surface 32. In FIGS. 4a and 4b, the path of the light beam is illustrated by the solid line L1.

Entering the first beam splitter 63, the light beam approaches the polarization film 36 at the Brewster angle as noted above.

The polarization film 36, which is illustrated by oblique lines in FIG. 4a, causes the light beam along path L1 to diverge into two components, a P component and an S component. In FIG. 4a, those two components proceed along paths which are shown employing a single dotted line L2 for the P component and a double dotted line L3 for the S component. The two components have different polarizations but have substantially the same optical energies.

After the divergence, as shown in FIG. 4a, the P component exits directly from the first beam splitter 63 at the transparent surface 33 along the path L2, toward the object A. On the other hand, the S component changes its direction at the polarization film 36 to follow the path L3 toward the reflection film 37. Then the S component is reflected by the reflection film 37. After the reflection, the S component exits from the first beam splitter 63 through the transparent surface 33 toward the second beam splitter 64 along the path L3.

Of the two components, only the P component passes through the object A. Passing through, the P component has its optical energy reduced, mainly because of the dust or soil contained in the atmosphere of the object A.

The degree of reduction of the P component depends on the optical transmission factor ($\tau$) of the object A. The parameter ($\tau$) will be described later.

Passing through the object A, the P component reaches the surface 143 of the fourth beam splitter 74, in the transmitter/receiver unit 70 on the opposite side beyond the object A. Then the P component passes substantially straight through the second beam splitter 74, to reach the photo-detector 75, which is also in the transmitter/receiver unit 70.

In response to the P component, the photo-detector 75 generates voltage signal pulses of amplitude $E_{20}$ at the times $t_1, t_3, t_5, t_7, \ldots$, each of which is designated by reference character 61P in FIG. 6. The voltage $E_{20}$ of the signal is in proportion to the optical energy of the P component as it reaches the photo-detector 75.

Meanwhile, as shown in FIG. 4a, the S component having diverged from the P component at the first beam splitter 63, enters the second beam splitter 64 along path L3 at the transparent surface 43. Then, the S component passes through the polarization film 47, and is reflected at the reflection film 48 attached to the surface 45. After the reflection, the S component again approaches the polarization film 47, and is reflected so as to exit the second beam splitter 64 at transparent surface 44.

Next, the S component reaches the photo-detector 65 in the transmitter/receiver unit 60.

In response to the S component, the photo-detector 65 generates a voltage signal of voltage $E_{1S}$ at the times $t_1, t_3, t_5, t_7, \ldots$, each of which is designated by reference character 61S in the FIG. 6. The voltage $E_{1S}$ is in proportion to the optical energy of the S component as it reaches the photo-detector 65.

On the other hand, a similar operation is carried out on the right side of the apparatus. That operation will be described hereinafter.

Figure 5A:
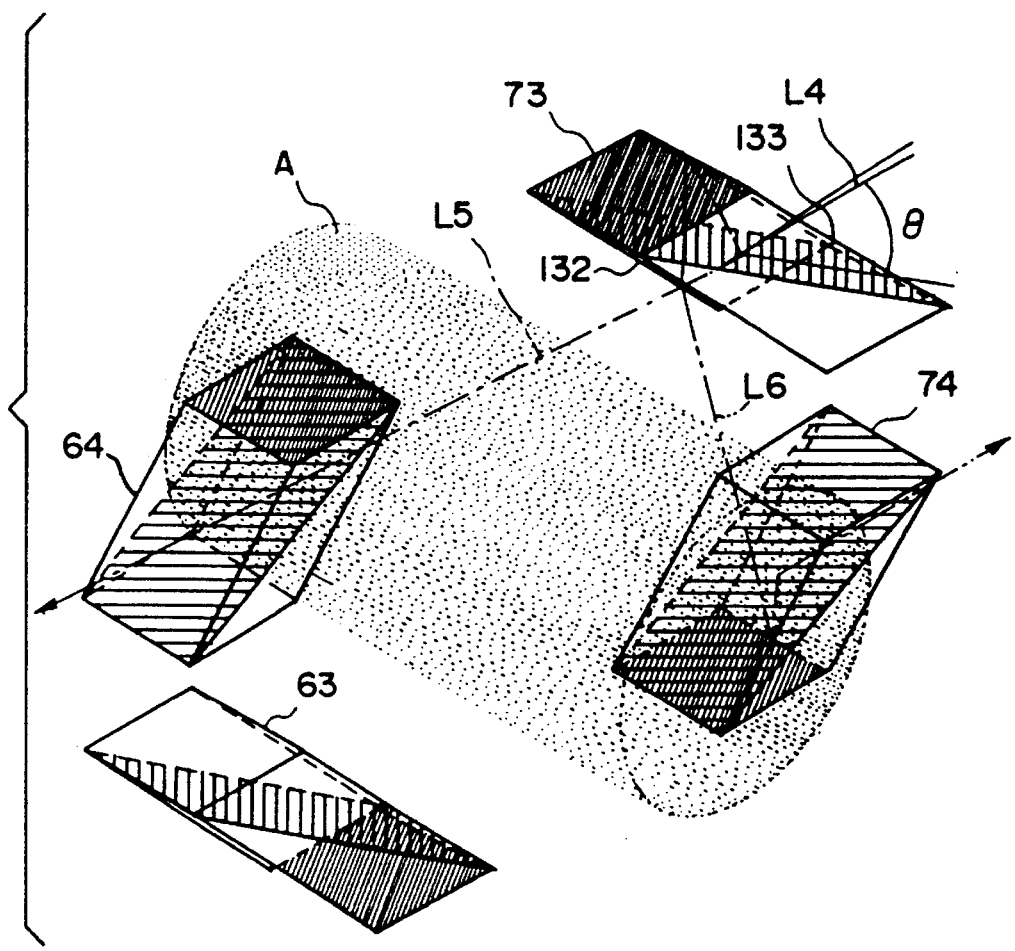
FIGS. 5a and 5b show the light beam paths of the P component and S component being emitted from the light source 71.
Figure 5B:
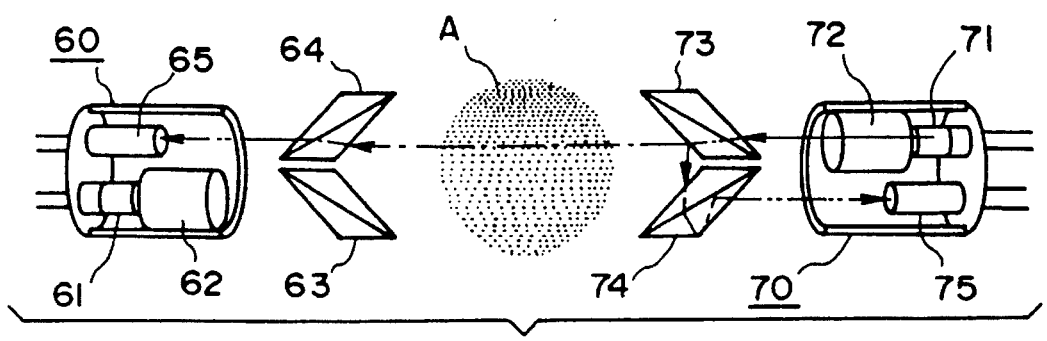

FIGS. 5a and 5b show the path of the light beam being emitted from the light source 71. The light beam being emitted from the light source 71 has a single narrow wavelength band. It is preferably a nondiffused beam, such as a laser beam.

The light beam enters the lens, assembly 72 and is output as a parallel light beam.

The lens assembly 72 also restricts the light beam diameter to be smaller than the effective diameter of the first or second beam splitter 73 or 74. The restriction helps to prevent the light beam from diffusing, when the light beam enters the beam splitters 72 and 73.

Upon exiting the lens assembly 72, the light beam enters the first beam splitter 73 at the transparent surface 133. In FIGS. 5a and 5b, the light beam path is illustrated by solid line L4.

Entering the third beam splitter 73, the light beam approaches the polarization film 136 at the Brewster angle θ. The Brewster angle θ is the same as noted above in the explanation of the beam splitter 63.

The polarization film 136 causes the light beam to diverge into two components, a P component and an S component. In FIG. 5a, those two components proceed along paths which are shown employing a single dotted line L5 for the P component and a double dotted line L6 for the S component. The two components have different polarizations, but have substantially the same optical energies.

After the divergence, the P component exits directly from the third beam splitter 73 through the transparent surface 132, toward the object A. On the other hand, the S component changes its direction at the polarization film 136 toward the surface 134. Then the S component is reflected by the reflection film attached to the surface 134. After the reflection, the S component exits from the third beam splitter 73 through the transparent surface 132 toward the fourth beam splitter 74.

Of the two components, only the P component passes through the object A. Passing through the object A, the P component has its optical energy reduced, mainly because of the dust or soil contained in the atmosphere of the object A.

The percentage reduction of the P component depends on the optical transmission factor (τ) of the object A. The parameter (τ) will be described later.

Passing through the object A, the P component reaches the second beams splitter 64 in the transmitter/receiver unit 60 on the opposite side of the apparatus. The P component passes substantially straight through the second beam splitter 64, to reach the photo-detector 65, which is also in the transmitter/receiver unit 60.

In response to the P component, the photo-detector 65 generates a voltage signal of amplitude $E_{10}$. The voltage $E_{10}$ is in proportion to the optical energy of the P component as it reaches the photo-detector 65.

Meanwhile, the S component, having diverged from the P component at the third beam splitter 73, enters the fourth beam splitter 74 at the transparent surface 143. Then, the S component passes through the polarization film 147, and is reflected at the reflection film 148 attached to the surface 145. After reflection, the S component again approaches the polarization film 147, and is reflected so as to exit the fourth beam splitter 74 at the transparent surface 144.

Next, the S component reaches the photo-detector 75 in the transmitter/receiver unit 70.

In response to the S component, the photo-detector 75 generates a voltage signal of amplitude $E_{2S}$. The voltage $E_{2S}$ is in proportion to the optical energy of the S component as it reaches the photo-detector 75.

Employing the four voltage amplitudes $E_{1S}$, $E_{10}$, $E_{2S}$ and $E_{20}$ as parameters, the optical transmission (τ) is defined as follows:

$$(\tau) = \sqrt{\frac{E_{10} \times E_{20}}{E_{1S} \times E_{2S}}} \quad (1)$$

When both of the P components do not have their optical energies reduced in the object A, $$E_{10} \cdot E_{20} = E_{1S} \cdot E_{2S} \therefore (\tau) = 1 \quad (2)$$

In the case where the P components reduce their optical energies in the object A from 1 to τ (<1), $$(\tau) = \sqrt{\frac{\tau E_{10} \times \tau E_{20}}{E_{1S} \times E_{2S}}} \quad (3)$$

because the voltages of the signals of the photo-detectors 65 and 75 are reduced in proportion to the reduced optical energies of the P components.

In addition, it is indispensable for calibrating the apparatus to check the signals of the photo-detectors 65 and 75 for span/zero calibration.

In the optical transmission measurement apparatus, the surfaces 33, 43, 132 and 143 in the beam splitters 63, 64, 73, and 74 respectively will be contaminated by the object A.

So, designating the optical transmission factors of the beam splitters 63, 64, 73, and 74 as $d_{11}$, $d_{12}$, $d_{21}$, $d_{22}$, parameters $E_{1S}$, $E_{10}$, $E_{2S}$, and $E_{20}$ respectively will be re-explained as follows:

$$E_{1S} = d_{11} \cdot d_{12} \cdot i_1 \cdot S_1 \quad (4)$$

$$E_{10} = d_{21} \cdot d_{12} \cdot k_{21} i_2 \cdot k_{11} S_1 \cdot \tau \quad (5)$$

$$E_{2S} = d_{22} \cdot d_{21} \cdot i_2 \cdot S_2 \quad (6)$$

$$E_{20} = d_{11} \cdot d_{22} k_{12} i_1 \cdot k_{22} S_2 \cdot \tau \quad (7)$$

where $k_{12}$ is a constant which indicates the ratio of the optical energy of the P component to the optical energy of the S component as these components are emitted from the first beam splitter 63, having diverged from each other at the first beam splitter 63;

$k_{21}$ is a constant which indicates the ratio of the optical energy of the P component to the optical energy of the S component as these components are emitted from the third beam splitter 73, having diverged from each other at the third beam splitter 73;

$k_{11}$ is a constant which indicates the ratio of the percentage of the optical energy of the P component that is retained while passing through the second beam splitter 64, to the percentage of the optical energy of the S component that is retained while passing through the second beam splitter 64;

$k_{22}$ is a constant which indicates the ratio of the percentage of the optical energy of the P component that is retained while passing through the fourth beam splitter 74 to the percentage of the optical energy of the S component that is retained while passing through the fourth beam splitter 74;

$k_{12} i_1$ is the optical energy of the P component upon being emitted from the first beam splitter 63, having diverged from the S component at the first beam splitter 63;

$k_{21} i_2$ is the optical energy of the P component upon being emitted from the third beam splitter 73, having diverged from the S component at the third beam splitter 73;

$S_1$ is a constant for converting the optical energy entering to the photo-detector 65 into the voltage signal; and
S$_2$ is a constant for converting the optical energy entering
to the photo-detector 75 into the voltage signal.

Employing the equation above, the optical transmission factor is transformed according to the following:

$$\sqrt{\frac{E_{10} \times E_{20}}{E_{1S} \times E_{2S}}} = \qquad (8)$$

$$\sqrt{\frac{d_{21}d_{12}k_{21}i_2k_{11}S_1\tau \times d_{11}d_{22}k_{12}i_1k_{22}S_2\tau}{d_{11}d_{12}i_1S_1 \times d_{21}d_{22}i_2S_2}} = \sqrt{k_{11}k_{12}k_{21}k_{22}} \times \tau$$

The procedure described above is a basic optical transmission measurement procedure of the embodiment; however, a similar but somewhat different procedure will be carried out for the calibration. The procedures for the span calibration and the zero calibration will be described hereinafter.

In the span calibration, the reflection mirror block 100 is slid into the light beam path. Other operations are the same as explained above, as a whole.

As shown in FIG. 3, the light source 61 intermittently emits light beam pulses in the transmitter/receiver unit 60 with a constant optical energy. On the other hand, the other light source 71 also intermittently emits light beam pulses in the transmitter/receiver unit 70, during time periods in which there is no light emission from the light source 61.

As is apparent from the explanation above or from the FIG. 6, it is during less than half of the total time period that each of the light source emits a light beam. And the light sources 61 and 71 never emit light beams simultaneously.

To simplify the explanation, a best example of the essential operation will be described hereinafter, as to the left side of the object A first. Of course, the same or similar operation will be carried out on the other side of the object A.

The light beam being emitted from the light source 61 has a single narrow wavelength band. It is preferably a nondiffused beam, such as a laser beam.

The light beam enters the lens assembly 62 and is output as a parallel light beam.

The lens assembly 62 also restricts the light beam diameter to be smaller than the effective diameter of the first or second beam splitter 63 or 64.

Being emitted from the lens assembly 62, the light beam passes through the first beam splitter 63, and approaches the first reflection mirror 101 at an angle of about 45°. Then the first reflection mirror 101 fully reflects the light beam so that the light beam retains all of its optical energy as it was emitted from the lens assembly 62.

In order to assure full reflection, the reflection mirror block 100 is preferably kept away from the object A to keep the mirror surfaces of the two reflection mirrors 101 and 102 from being contaminated.

Being reflected by the first reflection mirror 101, the light beam next approaches the second reflection mirror 102, again at an angle of about 45°. Then the second reflection mirror 102 fully reflects the light beam to keep all of its optical energy as it was reflected from the first reflection mirror 101.

After being reflected from the second reflection mirror 102, the reflected light beam will enter the photo-detector 65.

As stated, the light beam substantially keeps its optical energy from the light source 61 to the photo-detector 65.

Similarly, the light beam emitted from the light source 71 has a single narrow wavelength band. It is preferably a nondiffused beam, such as a laser beam.

The light beam enters the lens assembly 72 and is output as a parallel light beam.

The lens assembly 72 also restricts the light beam diameter to be smaller than the effective diameter of the third or fourth beam splitters 73 or 74.

Being emitted from the lens assembly 72, the light beam passes through the beam splitter 73, and approaches the first reflection mirror 105 at an angle of about 45°. Then the first reflection mirror 105 fully reflects the light beam so that the light beam retains all of its optical energy as it was emitted from the lens assembly 72.

In order to assure full reflection, the reflection mirror block 104 is preferably kept away from the object A to keep the mirror surfaces of the two reflection mirrors 105 and 106 from being contaminated.

Upon being reflected on the first reflection mirror 105, the light beam next approaches the second reflection mirror 106, again at an angle of about 45°. Then the second reflection mirror 106 fully reflects the light beam to keep all of its optical energy as it was reflected from the first reflection mirror 105.

After being reflected from the second reflection mirror 102, the reflected light beam will enter the photo-detector 75.

As stated, the light beam keeps substantially all of its optical energy from the light source 71 to the photo-detector 75.

Thus, the light beams emitted from the light sources 61 and 71 retain substantially all of their optical energies until they enter the photo-detectors 65 and 75.

As a result, the voltage signals which are generated by both of the photo-detectors 65 and 75 are the same as the signals would be in a case that the object A is completely clear and the light beams retain all of their optical energies while going through the object A. So these voltage signals have the maximum voltage on the measurement scale of the optical transmission.

The maximum voltage $E_{1R}$ from the photo-detector 65 should be equal to the voltage signals which would be detected if the object A were completely clear and the light beam were passed through it without being reduced in optical energy.

The maximum voltage $E_{1R}$ is given as the following:

$$E_{1R} = d_{11} \cdot d_{12} \cdot k_{12} \cdot i_1 \cdot k_{11} \cdot S_1 \qquad (9)$$

which should be equal to $E_{1S}$. In order to realize that condition:

$$k_{11} \cdot k_{12} = 1$$

must be satisfied.

Similarly, the maximum voltage $E_{2R}$ from the photo-detector 75 should be equal to the voltage signals which would be detected when the object A is completely clear and the light beam is never reduced in its optical energy as it passes through the object A.

The maximum voltage $E_{2R}$ is given as the following:

$$E_{2R} = d_{21} \cdot d_{22} \cdot k_{21} \cdot i_2 \cdot k_{22} \cdot S_2 \qquad (10)$$

which should be equal to $E_{2S}$. In order to realize that condition, $$k_{21} \cdot k_{22} = 1$$

must be satisfied.
Therefore, $$k_{11} \cdot k_{12} \cdot k_{21} \cdot k_{22} = 1$$

must be satisfied; if that condition is realized, then according to the above equation (8), $$\sqrt{\frac{E_{10} \times E_{20}}{E_{1S} \times E_{2S}}} = \sqrt{k_{11}k_{12}k_{21}k_{22}} \times \tau = \tau. \quad (11)$$

As described above, the reflection mirror blocks permit a span calibration to be made that simulates an imaginary clear object A of transmission factor $\tau=100\%$. This span calibration is enabled by inserting those blocks into the path of the P components, so that the reflection mirrors reflect the P components emitted from the transmitter/receiver units back to the same units. By providing those simulations, the parameters (calibration values) $E_{1R}$, $E_{2R}$, $E_{1S}$, $E_{2S}$ are obtained. Those parameters have been shown algebraically to enable the span calibration to be performed with the reflection mirror blocks.

Accordingly, the transmission factor $\tau$ determined during the calibration optionally may be determined for other degrees of transmission. For example, a pair of shutters which prevent the P components from returning to the transmitter/receiver units enables a zero calibration that simulates an imaginary opaque object A of transmission factor $\tau=0\%$. Similarly, providing a pair of neutral density optical filters instead of the shutters enable the half transmission calibration that simulates an imaginary half clear object A of transmission factor $\tau=50\%$.

I claim:

1. An optical transmission measurement apparatus for measuring optical transmission through an object, comprising:

a first transmitter/receiver unit comprising a first light source means, a first pair of first and second beam splitter means, and a first photo-detector means, wherein said first light source means emits a light beam of a predetermined polarization, said first beam splitter means causes the light beam to diverge into a first component and a second component which have different polarizations, and said second beam splitter means returns the first component to said first photo-detector means, a second transmitter/receiver unit comprising a second light source means, a second pair of third and fourth beam splitter means, and a second photo-detector means, wherein said second light source means emits a light beam of a predetermined polarization, said third beam splitter means causes the light beam to diverge into a third component and a fourth component which have different polarizations, and said fourth beam splitter means returns the third component to said second photo-detector means, first reflection mirror block means which is movable into and out of the light beam path of the second component, and second reflection mirror block means which is movable into and out of the light beam path of the fourth component, wherein said first and second units and said first and second reflection mirror block means are oriented and arranged so that when said first reflection mirror block means is in the light beam path of the second component, the second component is reflected at said first reflection mirror block means to enter said first photo-detector means through said second beam splitter means, when said second reflection mirror block means is in the light beam path of the fourth component, the fourth component is reflected at said second reflection mirror block means to enter said second photo-detector means through said fourth beam splitter means, when the first reflection mirror block means is out of the light path of the second component, the second component enters said second photo-detector means through the object and said fourth beam splitter means, and when the second reflector mirror block means is out of the light path of the fourth component, the fourth component enters said first photo-detector means through the object and said second beam splitter means.

2. An optical transmission measurement apparatus according to claim 1, wherein said first and second reflection mirror block means move out of the light beam paths of the second and fourth components when the apparatus measures the optical transmission factor of the object.

3. An optical transmission measurement apparatus according to claim 2, further comprising means for performing a calibration based on the first through fourth components upon detection thereof by said first and second photo-detector means while said first and second reflection mirror block means are in the light beam paths of the second and fourth components.

4. An optical transmission measurement apparatus according to claim 3, wherein said apparatus performs the calibration when said first reflection mirror block means reflects the second component and said second reflection mirror block means reflects the fourth component.

5. An optical transmission measurement apparatus according to claim 1, further comprising means for performing a calibration based on the first through fourth components upon detection thereof by said first and second photo-detector means while said first and second reflection mirror block means are in the light beam paths of the second and fourth component.

6. In a method for calibrating an optical transmission measurement apparatus having means for splitting a first light bean into first and second components which have different polarizations, a first photo-detector means which detects the first component, means for splitting a second light beam into third and fourth components which have different polarizations, and a second photo-detector means which detects the third component, wherein the second and fourth components are transmitted through an object and detected by the second and first photo-detector means respectively to permit the apparatus to measure the transmittance of the object according to a percentage of light reaching the object that passes therethrough, the improvement comprising the steps of:

transmitting the second component in addition to the first component to the first photo-detector means without either of the first and second components passing through the object, and transmitting the fourth component in addition to the third component to the second photo-detector means without either of the third and fourth components passing through the object; and detecting the second component in addition to the first component with the first photo-detector means, detecting the fourth component in addition to the third component with the second photo-detector means, and producing calibration signals based on the detected first through fourth components, the calibration signals being indicative of at least one calibration parameter for use in determining the percentage of the light reaching the object that passes through the object when light is transmitted through the object.

7. A method according to claim 6; wherein said step of transmitting includes the steps of
moving a first reflecting surface into a path of the second component so as to reflect the second component toward the first photo-detector means, and
moving a second reflecting surface into a path of the fourth component so as to reflect the fourth component toward the second photo-detector means.

8. An optical transmission measurement apparatus for measuring optical transmission through an object, comprising:
a first transmitter/receiver, including
a first photo-detector,
means for emitting a first light beam of predetermined polarization,
means for splitting the first light beam into a first component and a second component of different polarizations, the second component propagating on a first path toward the object, and
means for returning the first component to the first photo-detector;
a second transmitter/receiver unit, including
a second photo-detector,
means for emitting a second light beam of predetermined polarization,
means for splitting the second light beam into a third component and a fourth component of different polarizations, the fourth component propagating on a second path toward the object, and
means for returning the third component to the second photo-detector;
first reflecting means, movable into and out of the first path, for reflecting the second component back to said first photo-detector through said means for returning the first component, when said first reflecting means is in the first path; and
second reflecting means, movable into and out of the second path, for reflecting the fourth component back to said second photo-detector through said means for returning the third component, when said second reflecting means is in the second path, the second component entering said second photo-detector through the object and the fourth component entering said first photo-detector through the object, when the first and second reflecting means are out of the first and second paths;
the first and second photo-detectors producing calibration signals indicative of calibration values, in response to the second and fourth components received thereby when said first reflecting means is in the first path and said second reflecting means is in the second path, the first and second photo-detectors producing further calibration signals indicative of further calibration values, in response to the first and third components.

9. An apparatus according to claim 8, wherein the further calibration signals are produced when said first reflecting means is not in the first path and said second reflecting means is not in the second path.

10. An apparatus according to claim 8, wherein the further calibration signals and the calibration signals produced in response to the second and fourth components are produced at different times.

11. An apparatus according to claim 8, wherein the splitting means and returning means of said first unit are respectively a first beam splitter and a second beam splitter, and wherein the splitting means and returning means of said second unit are respectively a third beam splitter and a fourth beam splitter.

12. An apparatus according to claim 11, wherein each of said first and second reflecting means comprises a respective block and two mirrors, said two mirrors having reflective surfaces, said two mirrors being fixed to the block so that the reflective surfaces are perpendicular to each other and are oriented 45° to the first and second paths.

13. An apparatus according to claim 8, wherein each of said first and second reflecting means comprises a respective block and two mirrors, said two mirrors having reflective surfaces, said two mirrors being fixed to the block so that said reflective surfaces are perpendicular to each other and are oriented 45° to the first and second paths.

14. An apparatus according to claim 8, wherein the photo-detector, emitting means, splitting means, and returning means of each of the first and second units are aligned so that when the first and second reflecting means are out of the first and second paths, the second component enters said second photo-detector through the object and the fourth component enters said first photo-detector through the object.

15. A method of calibrating an optical transmission measuring apparatus, comprising the steps of:
emitting a first light beam of predetermined polarization;
splitting the first light beam into a first component and a second component of different polarizations;
directing the second component on a first path toward an object;
directing the first component away from the object to a first photo-detector;
emitting a second light beam of predetermined polarization;
splitting the second light beam into a third component and a fourth component of different polarizations;
directing the fourth component on a second path toward the object;
directing the third component away from the object to a second photo-detector;
reflecting the second component from a first mirror block disposed at a first position between the first photo-detector and the object, back to the first photo-detector, such that the second component does not pass through the object;
reflecting the fourth component from a second mirror block disposed at a second position between the second photo-detector and the object back to the second photo-detector, such that the fourth component does not pass through the object;
in the first and second photo-detectors, producing calibration signals indicative of calibration values, in response to the first and third components and the reflected second and fourth components; and
measuring the optical transmission of the object, including the steps of:
a. holding the first and second mirror blocks away from the first and second positions so that the second and fourth components do not reflect therefrom,
b. during said step a passing the second component through the object to the second photo-detector and passing the fourth component through the object to the first photo-detector; and c. after said step b, detecting the second component with the second photo-detector and detecting the fourth component with the first photo-detector.

16. A method according to claim 15, wherein the calibration signals are voltages indicative of the expected optical energies of the light beams upon detection after passing through a totally clear object in place of the object toward which the first and second paths extend.

* * * * *